(12) United States Patent
Matthis et al.

(10) Patent No.: US 7,335,202 B2
(45) Date of Patent: Feb. 26, 2008

(54) IMPLANT HAVING A SHAFT AND A HOLD ELEMENT CONNECTED THEREWITH FOR CONNECTING WITH A ROD

(75) Inventors: Wilfried Matthis, Weisweil (DE); Lutz Biedermann, VS-Villingen (DE); Jürgen Harms, Karlsruhe (DE)

(73) Assignee: Biedermann Motech GmbH (DE)

( * ) Notice: Subject to any disclaimer, the term of this patent is extended or adjusted under 35 U.S.C. 154(b) by 66 days.

(21) Appl. No.: 10/726,177

(22) Filed: Dec. 1, 2003

(65) Prior Publication Data

US 2004/0186474 A1  Sep. 23, 2004

(30) Foreign Application Priority Data

Dec. 2, 2002  (DE) ................ 102 56 095

(51) Int. Cl.
*A61B 17/70* (2006.01)

(52) U.S. Cl. ...................................... 606/61
(58) Field of Classification Search ............ 606/61, 606/72–73
See application file for complete search history.

(56) References Cited

U.S. PATENT DOCUMENTS

| | | | |
|---|---|---|---|
| 5,005,562 A | | 4/1991 | Cotrel |
| 5,176,680 A | * | 1/1993 | Vignaud et al. ............ 606/61 |
| 5,443,467 A | * | 8/1995 | Biedermann et al. ......... 606/65 |
| 5,520,689 A | * | 5/1996 | Schlapfer et al. ............ 606/61 |
| 5,681,319 A | * | 10/1997 | Biedermann et al. ....... 606/104 |
| 5,782,833 A | * | 7/1998 | Haider ...................... 606/61 |
| 6,063,090 A | * | 5/2000 | Schlapfer .................. 606/61 |
| 6,074,391 A | * | 6/2000 | Metz-Stavenhagen et al. ............. 606/61 |
| 6,224,598 B1 | * | 5/2001 | Jackson ..................... 606/61 |
| 6,296,642 B1 | * | 10/2001 | Morrison et al. ............ 606/61 |
| 6,368,321 B1 | * | 4/2002 | Jackson ..................... 606/61 |
| 6,371,957 B1 | * | 4/2002 | Amrein et al. .............. 606/61 |
| 6,458,132 B2 | * | 10/2002 | Choi ......................... 606/61 |
| 6,471,705 B1 | * | 10/2002 | Biedermann et al. ........ 606/61 |
| 6,485,494 B1 | * | 11/2002 | Haider ...................... 606/73 |
| 6,626,908 B2 | * | 9/2003 | Cooper et al. .............. 606/61 |
| 6,723,100 B2 | * | 4/2004 | Biedermann et al. ........ 606/73 |
| 6,786,903 B2 | * | 9/2004 | Lin ........................... 606/23 |

(Continued)

FOREIGN PATENT DOCUMENTS

| | | |
|---|---|---|
| DE | 0 614 649 A1 | 9/1994 |
| DE | 199 12 364 A1 | 10/2000 |
| EP | 1 219 255 A1 | 7/2002 |
| EP | 1 323 391 A2 | 7/2003 |
| WO | WO 00/27297 | 5/2000 |

*Primary Examiner*—Eduardo C. Robert
*Assistant Examiner*—Michael B Priddy
(74) *Attorney, Agent, or Firm*—Christie, Parker & Hale, LLP.

(57) ABSTRACT

An implant is described having a shaft and a holding element connected therewith for connecting with a rod. A recess is provided in the holding element that includes a U-shaped cross section for accommodation of the rod and two free legs at one end which include an inner thread. A closure element fixes the rod inserted into the U-shaped recess. The closure element has an outer thread cooperating with the inner thread of the legs. An abutment at or in the holding element limits tilting of the closure element about the rod at the time of final tightening of the closure element in the holding element.

24 Claims, 4 Drawing Sheets

U.S. PATENT DOCUMENTS

| | | |
|---|---|---|
| 6,869,433 B2 * | 3/2005 | Glascott ...................... 606/73 |
| 6,905,500 B2 * | 6/2005 | Jeon et al. .................... 606/61 |
| 6,918,911 B2 * | 7/2005 | Biedermann et al. ......... 606/61 |
| 2001/0001119 A1 * | 5/2001 | Lombardo ................... 606/73 |
| 2002/0138076 A1 | 9/2002 | Biedermann et al. |
| 2002/0151900 A1 * | 10/2002 | Glascott ...................... 606/73 |
| 2003/0125741 A1 | 7/2003 | Biedermann et al. |

* cited by examiner

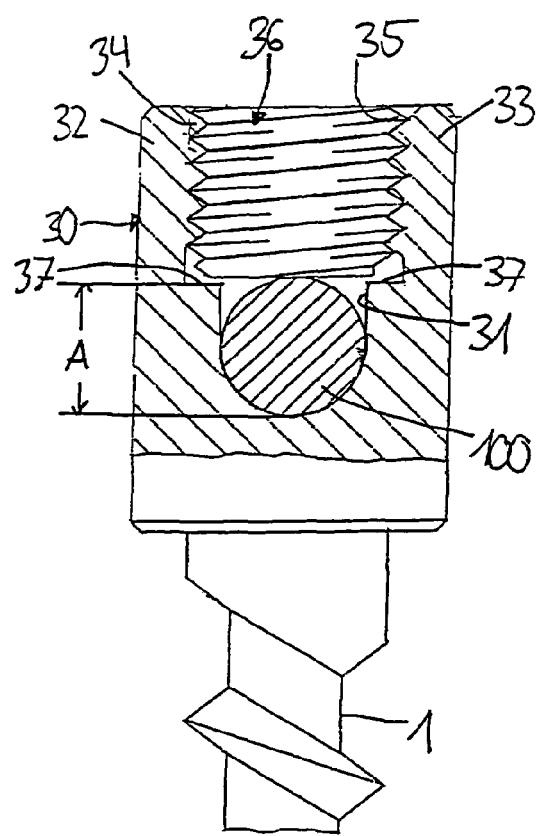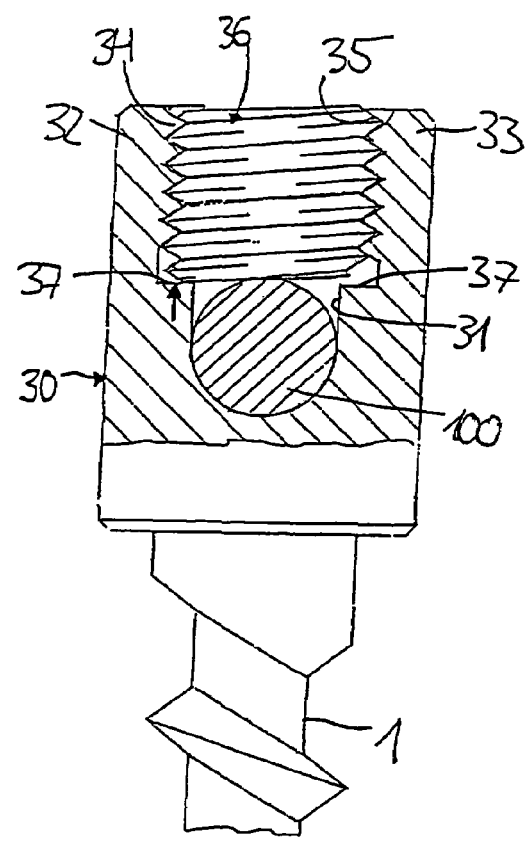
Fig. 5
Fig. 6

US 7,335,202 B2

IMPLANT HAVING A SHAFT AND A HOLD ELEMENT CONNECTED THEREWITH FOR CONNECTING WITH A ROD

FIELD OF THE INVENTION

The invention relates to an implant to be used in spine or trauma surgery, the implant having a shaft and a holding element connected therewith for connecting with a rod, wherein the holding element comprises a recess having a U-shaped cross section for receiving the rod and two free legs at one end which have an inner thread and a closure element for fixation of the rod inserted into the U-shaped recess, the closure element comprising an outer thread cooperating with the inner thread of the legs.

BACKGROUND OF THE INVENTION

EP 0 614 649 B1 describes a polyaxial bone screw with a receiver member with a nut to be screwed onto the receiver member for securing a rod.

If the thread of the receiver member and of an inner screw is a metric thread, force components in radial direction of the cylindrical receiver member occur when screwing in the inner screw, which could cause splaying of the legs of the receiver member resulting in a loosening of the inner screw.

Implants are known which employ only an inner screw for fixation of the rod, whereby a specific shape of the thread is provided for reducing the forces acting radially outward when screwing in. For example, U.S. Pat. No. 5,005,562 describes an implant having a receiver member, wherein the shape of the thread of the receiver member and the inner screw is formed as saw tooth thread, whereas WO 00/27297 describes the use of a thread with a negative angle of the load flank.

Such implants that have thin side flanks of the receiver member, however, encounter a problem when using only an inner screw for fixation without an additional securing via a nut to be screwed on or a cap covering the legs of the receiver member at the outside or a ring or the like. The problem is illustrated by means of FIG. 7, which shows schematically a polyaxial bone screw similar to that shown in EP 0 614 649 B1, but without the external cap or nut. As shown in FIG. 7, there is a screw element 101 having a spherical segment-shaped head 102, which is held in a receiver member 103 having a U-shaped recess for insertion of the rod 100. A pressure element 104 acts upon the spherical segment-shaped head 102 and, for fixation of the rod and of the head, an inner screw 105 with a metric thread is provided which can be screwed into the receiver member 103. At the time of final tightening of the inner screw with high torque, the inner screw tilts about the rod support surface or rotates about the rod such that a torsional force acts upon the legs of the receiver member distorting the same against each other. This results in an asymmetric splaying and deformation of the thread receiving parts resulting in the possibility that the inner screw can slide out of the lower left and the upper right turn shown by a circle in FIG. 7, respectively, and the respective turn may be skipped.

To avoid this, the inner screw should be tightened with reduced torque which, however, impairs the retention force. Further, the problem also can be reduced, if a wall of the receiver member is very thickly dimensioned, which is, however, an obstacle to the requirement of a compact implant design.

The problem of tilting of the inner screw at the time of final tightening which has been described is independent from the form of the used thread.

It is desirable to provide an element of the type described which allows a reliable fixation of the rod and at the same time makes a compact design possible.

SUMMARY OF THE INVENTION

The present invention provides an implant having a shaft (1) and a holding element (3; 30) connected therewith for connecting with a rod (100), wherein the holding element (3; 30) comprises a recess having a U-shaped cross section for receiving the rod and two free legs (7, 8; 32, 33) at one end which have an inner thread (9; 34) and a closure element (20; 36) for fixation of the rod inserted into the U-shaped recess, the closure element comprising an outer thread cooperating with the inner thread of the legs, wherein, at or in the holding element (3; 30), a securing device is provided which limits a tilting of the closure element about the rod at the time of final tightening of the closure element.

Alternative embodiments of the implants of the present invention further comprise one or more of the following features:

the securing device is formed by a support surface (12; 37) for cooperation with a section of the lower side of the closure element (20; 36) facing the rod;

the distance (A) between the bottom of the U-shaped recess to the support surface (12; 37) is smaller than the diameter (D) of the rod;

the distance (A) is smaller than the diameter (D) by an amount of approximately 1% to 7.5% of the diameter (D);

the securing device is formed as a projection (37) provided at the inside of the free legs (32, 33) of the holding element (30);

the shaft (1) and the holding element (30) are connected monoaxially, preferably formed in one piece;

the shaft (1) has a head (2) at one end being polyaxially connected to the holding element and wherein a pressure element (10) acting upon the head is provided for fixation of the angular position and wherein the securing device is provided at the pressure element (10);

the pressure element (10) comprises a U-shaped recess (14) corresponding to the recess of the holding element (3) and wherein the securing device is formed by the free edge (12) of the legs (15, 16) formed by the recess;

the distance (A) from the bottom of the U-shaped recess to the free end (12) of the pressure element is smaller than the diameter (D) of the rod; and/or the inner thread of the legs (7, 8; 32, 33) and the outer thread of the closure element (20; 36) is formed as metric thread or as saw tooth thread or as thread having a load flank having a negative angle or as a flat thread.

The construction of the implant in accord with the present invention is suitable, not only for polyaxial bone screws but also for monoaxial bone screws or hooks and is suitable for all forms of threads used for the receiver member and the inner screw. Implants in accord with the present invention are particularly advantageous for use with a rod having circular cross section.

The invention also provides a method for fixing a rod relative to a bone. The method comprises providing an implant as described above, connecting the implant to the bone, positioning the rod in the implant, and fixing the rod in the implant. In embodiments where the implant is a polyaxial screw, the method further comprises adjusting the angular position of the polyaxial screw element relative to the holding element and adjustment of the rod. In other embodiments where the implant is a polyaxial screw preferably comprising a screw element having a head with a recess in the head, the method further comprises assembling the screw elements and holding member of the implant, inserting a pressure member into the holding member, screwing the polyaxial screw into the bone using a driving tool that drives the screw by means of the recess in the head, and after positioning the rod, fixing the rod by tightening the closure element in the holding element.

In certain preferred embodiments, the fixing step includes tightening of the closure element by applying strong forces to tilt the closure element about the rod until stopped against further forward movement by the abutment.

Further features and advantages of the invention will become apparent to those skilled in the art from the description of embodiments and the accompanying Figures.

BRIEF DESCRIPTION OF THE DRAWINGS

FIG. 5: is an elevational view, partially in section, of a second embodiment of the invention in which the inner screw is not yet tightened;

FIG. 6: is an elevational view, partially in section, of the second embodiment of the invention in which the inner screw is tightened;

DETAILED DESCRIPTION OF THE INVENTION INCLUDING PREFERRED EMBODIMENTS

Figure 1:
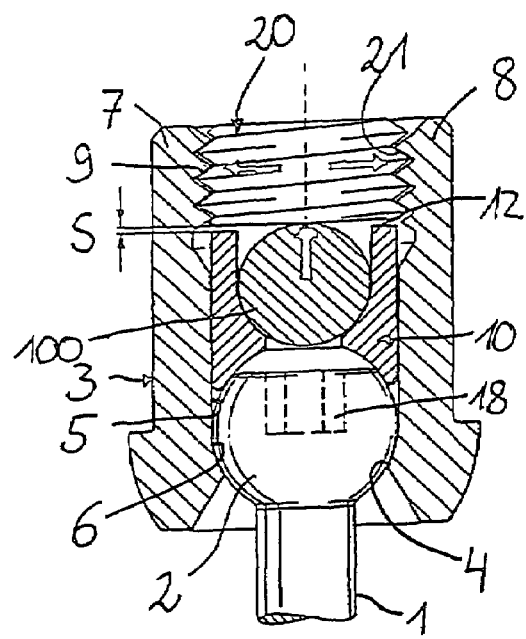
FIG. 1: is an elevational view, partially in section, of a first embodiment of the invention in which the inner screw is not yet tightened.

In the embodiment shown in FIGS. 1 to 4 an implant according to the present invention is formed as a polyaxial screw comprising a screw element having a threaded shaft 1 with a bone thread (not shown) and an integral spherical segment-shaped head 2. The head 2 is held within the receiver member 3. The receiver or holding member 3 has at its one end an axially symmetric first bore 4, the diameter of which is greater than that of the thread section of the shaft 1 and smaller than that of the head 2. Further, the receiver 3 comprises a coaxial second bore 5, which is open at the end opposite to the first bore 4 and the diameter of which is sufficiently large that the screw element can be passed through the open end with its threaded section going through the first bore 4 and with the head 2 held in a section 6 between the bottom of the second bore 5 and the first bore 4. The small coaxial section 6 is provided adjacent to the first bore 4 and is spherically shaped towards the open end of the second bore 5, wherein the radius of the spherically shaped section 6 is substantially the same as that of the spherical segment-shaped section of the head 2.

The receiver or holding member 3 further comprises in a conventional manner a U-shaped recess 3' arranged symmetrically with respect to the center of the part for accommodation of the rod 100, the bottom of which is directed towards the first bore 4 and by which the two free legs 7, 8 are formed. In a region adjacent to their free end, the legs 7, 8 comprise an inner thread 9 which is formed in this embodiment as a metric thread.

Further, a cylindrical pressure element 10 is provided having a first end 11, which faces the head 2 in a state where the pressure element is inserted into the receiver 3, and with a second end 12 opposite to the first end. The outer diameter of the pressure element is slightly smaller than that of the bore 5 of the receiver member, such that the pressure element is able to slide into the bore 5, i.e., it is displaceable in bore 5 towards the head 2.

The pressure element 10 further comprises at its first end 11 a spherical segment-shaped recess 13 enlarging towards the end, the radius of which is selected such that the pressure element partly encompasses the head 2 when it is inserted into the receiver.

Figure 2:
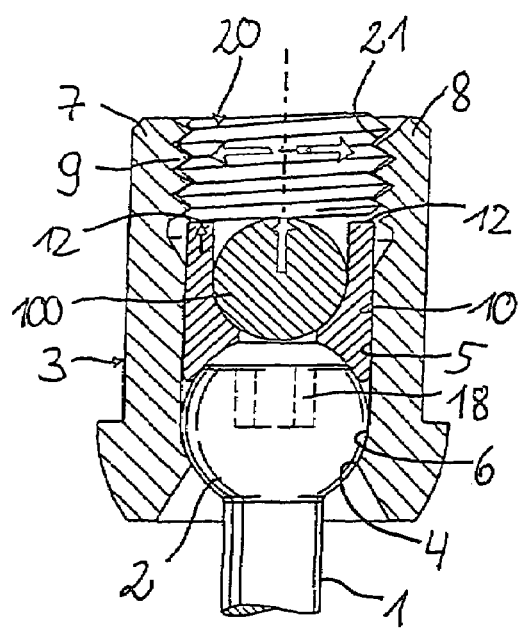
FIG. 2: is an elevational view, partially in section, of the first embodiment in which the inner screw is tightened.
Figure 3:
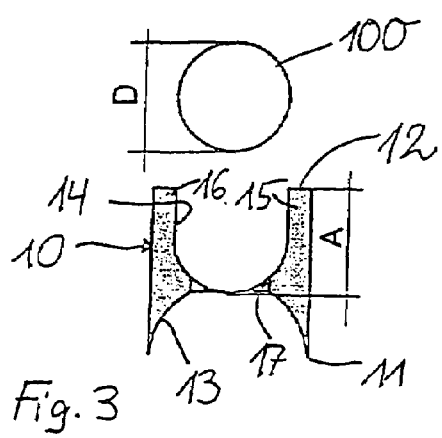
FIG. 3: is a schematic elevational representation of the pressure element in relation to the rod for the first embodiment.
Figure 4:
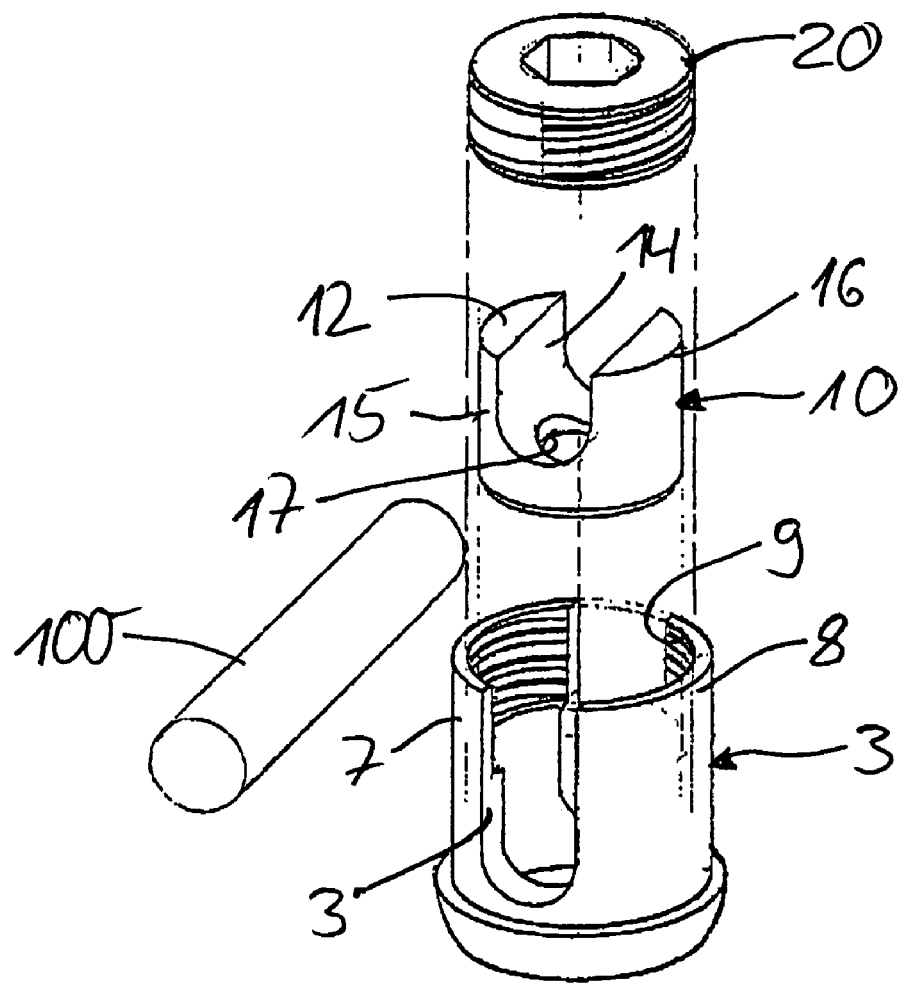
FIG. 4: is an exploded view of the first embodiment.
Figure 4:
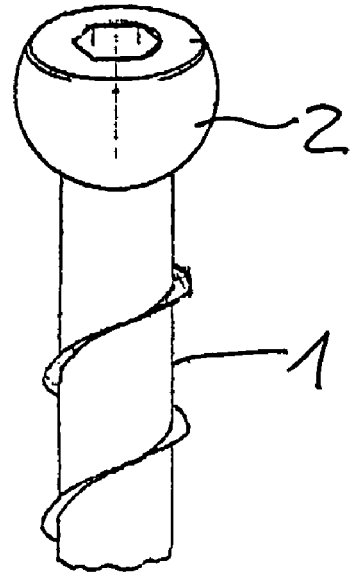

Further, the pressure element 10 is provided with a U-shaped recess 14 at the second end 12 opposite to the spherically-shaped recess 13, thereby forming two legs 15, 16. The dimensions of the U-shaped recess 14 of the pressure element are such that the recess forms a channel in which the rod 100 can be inserted. As illustrated in FIG. 2 and particularly shown in FIGS. 1 and 3, the depth A of the U-shaped recess 14, as seen in direction of the cylinder axis of the pressure element, is smaller than the diameter D of the rod 100 to be accommodated. In a state shown in FIG. 1, in which the pressure element 10 is inserted into the receiver and in which the rod 100 is inserted, the rod 100 protrudes by a distance or height S above the first end 12 formed by the free end of the legs 15, 16. The height S preferably is from about 1% to about 7.5% of the diameter D of the rod for the usual dimensions of the polyaxial screw implant.

The pressure element further comprises a central bore 17 extending therethrough and the diameter of which is sufficiently large that a screw-in tool for engaging with a recess 18 provided in the head 2 can be passed therethrough.

In addition, an inner screw 20 is provided as a closure element that has an outer thread 21 cooperating with the inner thread 9 of the legs 7, 8 of the receiver member and which is dimensioned such that the screw does not or does not substantially protrude above the receiver member in the screwed-in state when the screw 20 presses on the inserted rod 100. The inner thread 9 of the receiver is preferably dimensioned such that beginning from the free end of the legs 7, 8 it does not extend substantially deeper than the upper edge of the rod when the rod rests on the bottom of the U-shaped recess of the inserted pressure element.

In operation, first, the screw element is inserted into the receiver 3 until the head 2 contacts the spherical section 6. Then, the pressure element 10 is inserted and positioned in such a way that the U-shaped recess 3' of the receiver member and the U-shaped recess 14 of the pressure element 10 correspond. In this state the screw element is screwed into the bone by means of a drive tool engaging the recess 18 in head 2. Thereafter, the rod 100 is inserted and the closure element, inner screw 20, is screwed into the receiver element to contact rod 100. After adjustment of the angular position of the polyaxial screw element relative to the receiver and adjustment of the rod 100, the inner screw 20 is tightened to fix the rod and the angle of the screw element. Thus, at the beginning, the lower side of the inner screw 20 touches the rod only slightly whereby, between the lower side of the inner screw and the free second end 12 of the pressure element, there is then a gap of the size S as shown in FIG. 1. At this time the legs 7, 8 of the receiver can possibly be slightly splayed which is indicated by the arrows. At the time of final tightening of the inner screw 20 and of applying strong forces, the inner screw 20 tends to escape the pressure acting on it and to tilt about the rod, however, it is hindered because its lower edge is supported by the free end 12 of one of the legs 15, 16 of the pressure element 10 forming an abutment against further forward movement of the inner screw 20. In that way the influence of torsional forces at the time of final tightening is avoided and any further splaying of the legs of the receiver is prevented. Therefore, it is also possible to apply a higher torque at the time of final tightening and, thereby, generate a high retention force without having an excessive splaying of the receiver legs 7, 8 or tilting of the inner screw 20. Therefore, a skipping of one turn of the thread of the receiver by the inner screw is prevented. In the final state in which the inner screw is completely screwed in, the inner screw fixes the rod and fixes via the pressure element and the rod also the head 2.

There is a desired advantage that the thickness of the wall of the receiver member can be reduced because this design is more compact and the prevention of tilting of the inner screw at the time of tightening is highly safeguarded.

In the embodiment shown in FIGS. 5 and 6, the implant in accord with the present invention is formed as monoaxial bone screw. In this embodiment, a shaft 1 having a section with a bone thread is rigidly connected to a receiver or holding member 30 for accommodation of the rod 100. The receiver has a recess 31 with a U-shaped cross section, which is dimensioned sufficiently large that the rod 100 can be placed in and fits to the bottom of the recess. Due to the U-shaped recess 31, two free legs 32, 33 are formed which have an inner thread 34 adjacent to their free end, the inner thread cooperating with a corresponding outer thread 35 of an inner screw 36 (the closure element), which is to be screwed in between the legs for fixation of the rod 100.

As shown in FIG. 5, the U-shaped recess 31 has a channel width from the bottom until a height A which is slightly smaller than the diameter D of the rod to be received such that the rod is displaceable into the channel formed by the recess. Adjacent to this region and starting from the height A until the free end of the legs 32, 33, the inner diameter of the receiver 30 is larger than the diameter of the rod. Therefore, a shoulder or projection 37 is formed at the inside of each of the legs 32, 33, which forms an abutment for supporting the inner screw to avoid tilting thereof. The inward projection 37 can be formed, for example, as the undercut for the inner thread with a planar surface.

The operation and function of the implant illustrated by the second embodiment is similar to the first embodiment. As shown in FIG. 6, the abutment 37 acts as a support in case of tilting of the inner screw 36 and offers a counterforce (indicated by the small arrow) against the edge of the inner screw, which prevents a distortion of the legs at the time of tightening. Therefore, the same effects are achieved as by the first embodiment.

The invention has been described including the preferred embodiments thereof. However, it will be appreciated that those skilled in the art may make modifications and improvements within the spirit and scope of the invention.

As such, various alternative modifications of the embodiments described are possible. For example, instead of the metric thread of the receiver member and the inner screw, a saw tooth thread, a thread having a load flank with a negative flank angle or a flat thread can be provided. The latter is characterized in that both flanks of the thread enclose an angle of 90° with the screw axis. When using the thread forms as described, a splaying of the legs does not occur because there are no force components acting radially outwards. In spite of this, there is tilting at the time of final tightening of the inner screw and therefore torsional forces are produced which could lead to a deformation of the thread of the outer flanks of the receiver member. This is reliably prevented by using a structure in accord with the present invention together with the thread forms as described above.

The threads described can further be formed as right hand or left hand threads.

The inner screw can be formed as sleeve-like part with an outer thread and can have a continuous slit or a partial slit in axial direction.

Instead of the shaft having the bone thread, a hook can be provided.

What is claimed is:

1. An implant comprising:
   a rod;
   a shaft;
   a holding element connected with the shaft, wherein the holding element comprises a recess with a U-shaped cross section for receiving the rod, the recess forming two free legs having at one end thereof an inner thread;
   a closure element for fixation of the rod inserted into the U-shaped recess, the closure element having an outer thread cooperating with the inner thread of the legs and having a lower side which contacts the rod; and
   an abutment to limit a tilting of the closure element about the rod at the time of final tightening of the closure element in the holding element;
   wherein the closure element is movable from a first position spaced from the abutment wherein the lower side of the closure element contacts the rod to a second position wherein the lower side of the closure element directly contacts both the abutment and the rod.

2. The implant according to claim 1, wherein the abutment is a support surface for a section of the lower side of the closure element.

3. The implant according to claim 2, wherein the U-shaped recess has a bottom and the rod has a diameter, a distance from the bottom of the U-shaped recess to the support surface being smaller than the diameter of the rod.

4. The implant according to claim 3, wherein the distance is smaller than the diameter by an amount from about 1% to about 7.5% of the diameter.

5. The implant according to claim 1, wherein the abutment is an inward projecting surface on the inside of the free legs of the holding element.

6. The implant according to claim 1, wherein the shaft and the holding element are connected monoaxially.

7. The implant according to claim 6, wherein the shaft and the holding element are formed in one piece.

8. The implant according to claim 6, wherein the shaft and the holding element are a single continuous one piece part.

9. The implant according to claim 1, wherein the shaft has a head at one end that is polyaxially connected to the holding element,
   wherein the implant further comprises a pressure element having an end facing the closure element for acting upon the head to fix an angular position of the shaft relative to the holding element, and
   wherein the abutment is provided at the end of the pressure element.

10. The implant according to claim 9, wherein the pressure element comprises a U-shaped recess with a bottom corresponding to the U-shaped recess of the holding element, the U-shaped recess of the pressure element forming two free legs having a free end in a plane and wherein the abutment is formed by the free end.

11. The implant according to claim 10, wherein the rod has a diameter and wherein a distance from the bottom of the U-shaped recess of the pressure element to the free end of the pressure element is smaller than the diameter of the rod.

12. The implant according to claim 11, wherein the distance is smaller than the diameter by an amount from about 1% to about 7.5% of the diameter.

13. The implant according to claim 9, wherein the shaft comprises a screw element having a bone thread and a head and the pressure element is shaped such as to at least partly encompass the head of the screw element.

14. The implant according to claim 9, wherein the shaft comprises a screw element having a bone thread and a head and the pressure element includes a coaxial bore for inserting a screw-in tool to cooperate with the head of the screw element.

15. The implant according to claim 1, wherein the inner thread of the legs and the Outer thread of the closure element are formed as a thread selected from the group consisting of a metric thread, a saw tooth thread, a thread having a load flank having a negative angle, and a flat thread.

16. The implant according to claim 1, wherein the shall comprises a bone thread or a bone hook.

17. The implant according to claim 1, wherein the lower side of the closure element contacts the abutment at the time of final, tightening of the closure element in the holding element.

18. The implant according to claim 1, wherein the abutment is a surface of the free legs of the holding element projecting inwardly into the recess.

19. The implant according to claim 1, wherein the shaft has a head at one end that is polyaxially connected to the holding element,
wherein the implant further comprises a pressure element having an end facing the closure element for acting upon the head to fix an angular position of the shaft relative to the holding element, and
wherein the abutment is provided at the end of the pressure element and the lower side of the closure element contacts the end of the pressure element at the time of final tightening of the closure element in the holding element.

20. An implant comprising:
a rod;
a shaft having a head at one end that is polyaxially connected to a holding element, the holding element comprising a recess with a U-shaped cross section for receiving the rod, the recess forming two free legs having at one end thereof an inner thread;
a closure element for fixation of the rod inserted into the U-shaped recess, the closure element having an outer thread cooperating with the inner thread of the legs and having a lower side which contacts the rod;
a pressure element having an end facing the closure element for acting upon the head to fix an angular position of the shaft relative to the holding element; and
an abutment on the pressure element to limit a tilting of the closure element about the rod at the time of final tightening of the closure element in the holding clement;
wherein the closure element is movable from a first position spaced from the abutment wherein a lower side of the closure element contacts the rod to a second position wherein the lower side of the closure element directly contacts both the abutment and the rod.

21. A method of fixing a rod relative to a bone, the method comprising:
providing an implant comprising:
a rod;
a shaft;
a holding element connected with the shaft, wherein the holding element comprises a recess with a U-shaped cross section for receiving the rod, the recess forming two free legs having at one end thereof an inner thread;
a closure element for fixation of the rod inserted into the U-shaped recess, the closure element having an outer thread cooperating with the inner thread of the legs and having a lower side which contacts the rod; and
an abutment directly contacting the closure element to limit a tilting of the closure element about the rod at the time of final tightening of the closure element in the holding element;
connecting the implant to the bone;
positioning the rod in the implant; and
fixing the rod in the implant, wherein the fixing step includes tightening of the closure element by applying strong forces to tilt the closure element about the rod until stopped against further forward movement by the abutment.

22. The method according to claim 21, wherein the implant is a polyaxial screw and the method further comprises adjusting the angular position of the polyaxial screw relative to the holding and adjustment of the rod.

23. The method according to claim 21, wherein the implant is a polyaxial screw comprising a head with a recess in the head and the method further comprises:
assembling the polyaxial screw and holding element of the implant;
inserting a pressure member into the holding element;
screwing the polyaxial screw into the bone using a driving tool that drives the screw by means of the recess in the head; and
after positioning the rod, fixing the rod by tightening the closure element in the holding element.

24. The method of claim 21, further comprising moving the closure element into contact with the rod and into contact with the abutment.

* * * * *

UNITED STATES PATENT AND TRADEMARK OFFICE
CERTIFICATE OF CORRECTION

PATENT NO. : 7,335,202 B2
APPLICATION NO. : 10/726177
DATED : February 26, 2008
INVENTOR(S) : Wilfried Matthis It is certified that error appears in the above-identified patent and that said Letters Patent is hereby corrected as shown below:

On the Title Page

(54) Title, line 1            Delete "HOLD",
                              Insert --HOLDING--

In the Drawings

Figure 7:
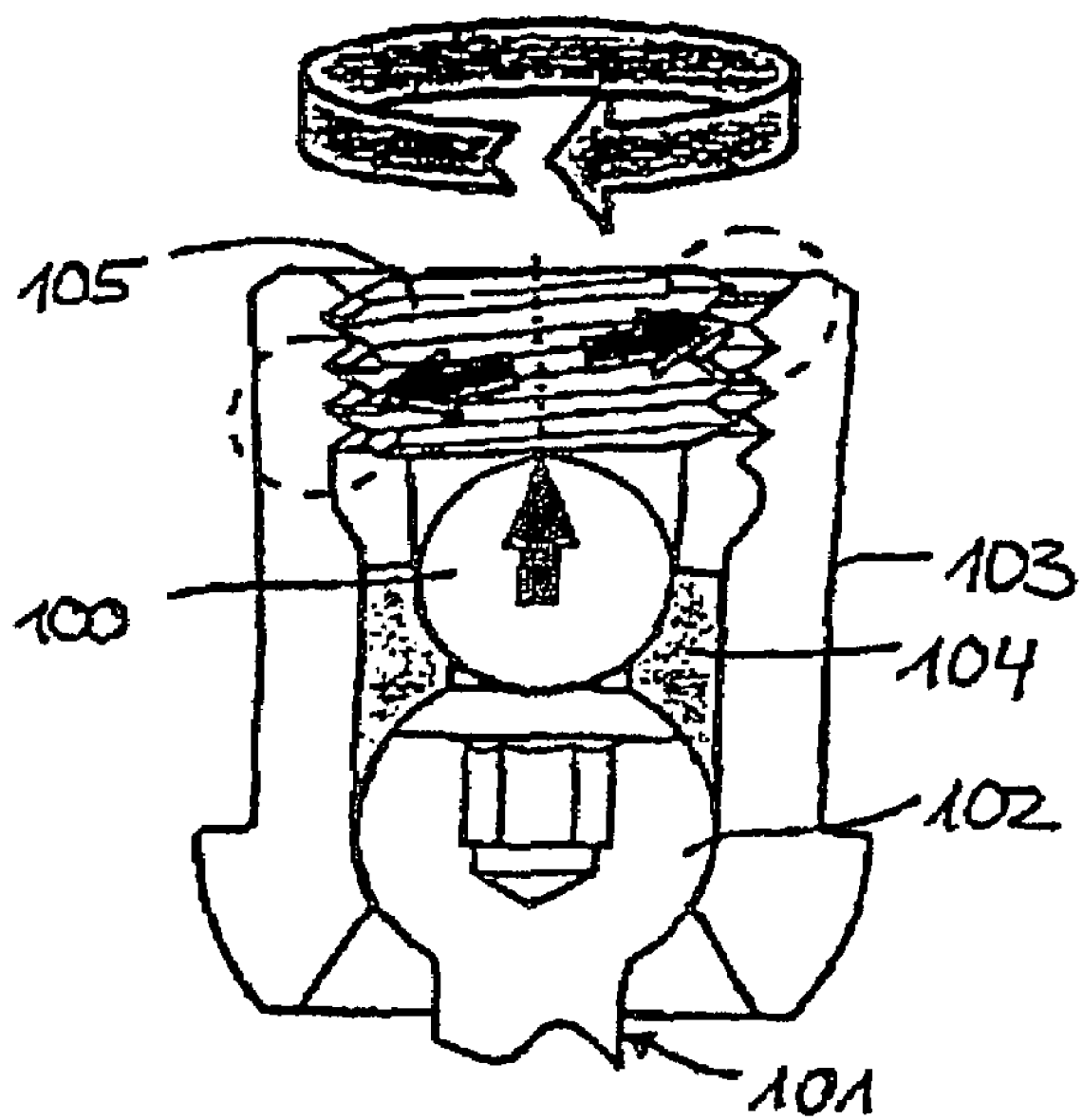
FIG. 7: is a schematic elevational view of a conventional polyaxial screw with inner screw at the time of final tightening of the inner screw.
Figure 7:
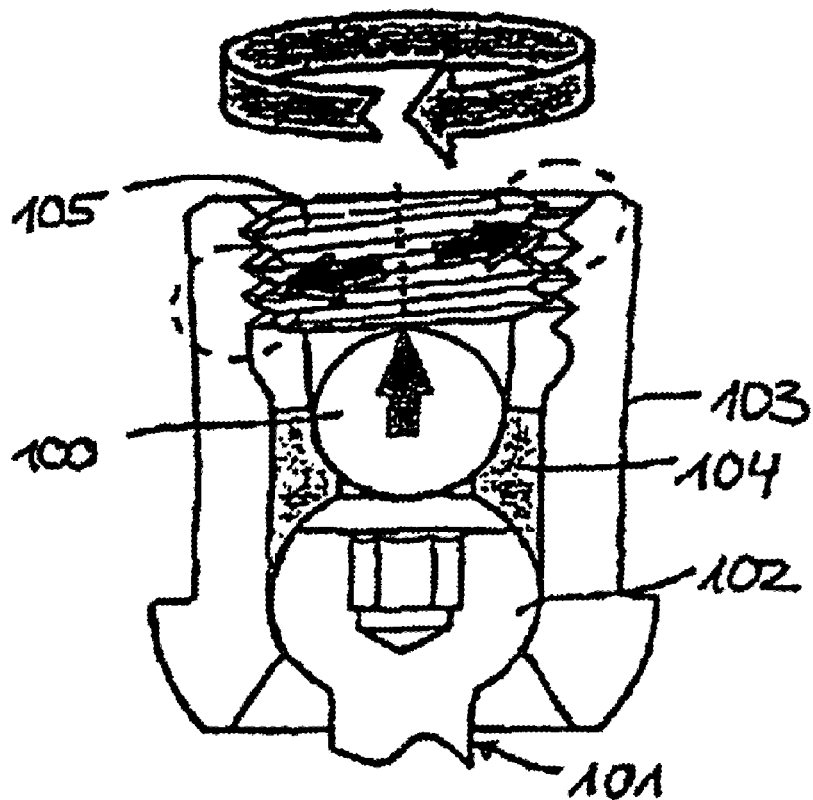

Fig. 7, Sheet 4 of 4          Delete Drawing Sheet 4 and substitute therefore
                              the Drawing Sheet, consisting of Fig. 7, as
                              shown on the attached page Column 1, line 1              Delete "HOLD",
                              Insert --HOLDING--

Column 6, line 23, Claim 1    Delete "clement",
                              Insert --element--

Column 7, line 20, Claim 15   Delete "Outer",
                              Insert --outer--

Column 7, line 24, Claim 16   Delete "shall",
                              Insert --shaft--

Column 7, line 28, Claim 17   Delete "final,",
                              Insert --final--

UNITED STATES PATENT AND TRADEMARK OFFICE
CERTIFICATE OF CORRECTION

PATENT NO. : 7,335,202 B2
APPLICATION NO. : 10/726177
DATED : February 26, 2008
INVENTOR(S) : Wilfried Matthis It is certified that error appears in the above-identified patent and that said Letters Patent is hereby corrected as shown below:

Column 8, lines 3-4, Claim 20        Delete "clement",
                                     Insert --element--

Signed and Sealed this

Eleventh Day of November, 2008

JON W. DUDAS
*Director of the United States Patent and Trademark Office*